US008802425B2

United States Patent
Ferrera

(10) Patent No.: US 8,802,425 B2
(45) Date of Patent: Aug. 12, 2014

(54) METHOD FOR THE HYPOTHERMIC PERFUSION OF A CARDIAC ORGAN, AND DEVICE FOR THE IMPLEMENTATION THEREOF

(75) Inventor: René Ferrera, Decines (FR)

(73) Assignees: Universite Claude Bernard Lyon I, Villeurbanne Cedex (FR); INSERM (Institut National de la Sante et de la Recherche Medicale), Paris Cedex (FR)

( * ) Notice: Subject to any disclaimer, the term of this patent is extended or adjusted under 35 U.S.C. 154(b) by 0 days.

(21) Appl. No.: 13/513,926

(22) PCT Filed: Dec. 8, 2010

(86) PCT No.: PCT/FR2010/052648
§ 371 (c)(1),
(2), (4) Date: Jul. 6, 2012

(87) PCT Pub. No.: WO2011/077024
PCT Pub. Date: Jun. 30, 2011

(65) Prior Publication Data
US 2012/0264104 A1 Oct. 18, 2012

(30) Foreign Application Priority Data
Dec. 11, 2009 (FR) .................................... 09 58878

(51) Int. Cl.
*A01N 1/02* (2006.01)
*A01N 1/00* (2006.01)

(52) U.S. Cl.
CPC ............ *A01N 1/0268* (2013.01); *A01N 1/0273* (2013.01); *A01N 1/0247* (2013.01)
USPC ...... 435/284.1; 435/1.2; 435/289.1; 600/334; 600/335

(58) Field of Classification Search
CPC ..... A01N 1/0247; A01N 1/02; A01N 1/0273; A01N 1/0205; A01N 1/0263; A01N 1/021; A01N 1/0221; A01N 1/0226
USPC .......... 435/1.2, 284.1, 283.1, 289.1; 600/334, 600/335
See application file for complete search history.

(56) References Cited

U.S. PATENT DOCUMENTS

| 3,877,843 | A | * | 4/1975 | Fischel | .......................... 417/394 |
| 5,385,821 | A | * | 1/1995 | O'Dell et al. | ................... 435/1.2 |
| 2005/0147958 | A1 | | 7/2005 | Hassanein et al. | |
| 2011/0212431 | A1 | * | 9/2011 | Bunegin et al. | ................ 435/1.2 |

FOREIGN PATENT DOCUMENTS

WO 2009/132018 10/2009

OTHER PUBLICATIONS

Safar et al. Disturbance of macro- and microcirculation: relations with pulse pressure and cardiac organ damage. Am J Physiol Heart Circ Physiol. 2007;293:H1-H7.*

* cited by examiner

*Primary Examiner* — Michael Hobbs
(74) *Attorney, Agent, or Firm* — Clark & Brody

(57) ABSTRACT

A device for hypothermic perfusion of a cardiac organ comprising a first sealed tank able to contain a physiological liquid, a second sealed tank communicating, in a sealed manner, with an internal volume of the first tank via a nozzle, a device for refrigerating the first tank and keeping the first tank at a substantially constant temperature and a device for intermittently pressurizing the internal volume of the first tank. The first tank communicates with the pressurizing device by way of a conduit connecting an interior of the first tank to the pressurizing device to permit pressurization of the internal volume of the first tank, and of the physiological liquid inside the first tank, in order to perform perfusion of the organ. The second tank comprises a safety element formed by an overflow outlet duct which communicates with the first tank and includes a non-return valve.

6 Claims, 1 Drawing Sheet

METHOD FOR THE HYPOTHERMIC PERFUSION OF A CARDIAC ORGAN, AND DEVICE FOR THE IMPLEMENTATION THEREOF

BACKGROUND OF THE INVENTION

The present invention relates to the field of removal and storage of organs with a view to their transplantation, both in humans and in animals.

More particularly, the invention relates to a method for hypothermic perfusion of a cardiac organ and to a perfusion device for carrying out the method.

Organ transplant operations, put simply, involve at least one defective organ in a living patient being replaced by the healthy and functional corresponding organ from a deceased person or, in the case of kidney transplants for example, from a living person who has agreed to donate one of his or her kidneys to a patient who is ill.

In practice, the organ or organs that are to be transplanted are removed from a donor and then stored immediately in a hypothermic state in appropriate storage devices for transporting them to the hospital establishment where the transplant operation is to be performed on the patient who is ill. This phase of storage of the transplant organs often proves critical.

One of the main problems encountered in transplantation procedures is the limited period of preservation of the transplants in a hypothermic state. Thus, for a heart transplant for example, the maximum acceptable duration between the removal of the transplant organ from the donor and its implantation in the recipient is considered to be from 4 to 6 hours. This very short time frame requires that all the participants in the transplantation procedure act with great urgency, from the personnel removing the organs to the personnel performing the transplantation itself, and including the personnel charged with transporting the organs. What is worse, this very brief period of viability of the organ between its removal and its transplantation obviously means that many transplantation operations cannot proceed because the distance between donor and recipient is too great.

Many technical proposals have hitherto been made for storing organs with a view to their transplantation.

In particular, in the first instance, there is the customary technique of organ preservation involving rapid cooling followed by cold immersion in a liquid. Unfortunately, this technique does not allow the organ to be preserved in good conditions of viability beyond 4 to 6 hours, especially in the case of a heart transplant for example. Beyond this storage period, considerable degradation is observed in the tissues of the organ that is to be transplanted.

Moreover, the literature available in the field of transplantation, particularly heart transplantation, specifies that perfusion greatly improves the conditions for survival of a heart transplant compared to preservation by immersion. However, the perfusion of heart transplants, permitting the transport of a beating heart, requires suitable apparatuses that take up a lot of space and are complex and that are provided with a system for recirculating the perfusate at body temperature and with an autonomous power source. For this reason, these apparatuses are often considered too expensive and too complex, and they have not hitherto been developed for practice in human medicine.

Document WO 2009/132018 A1 describes an organ perfusion device which is compact and involves pressurization of a liquid through the organ. However, this device pressurizes the organ itself through the effect of positive liquid pressures in the organ, which is thus "inflated" with perfusion liquid. This technique is damaging to the organic tissues and adversely affects their storage.

SUMMARY OF THE INVENTION

In light of the disadvantages or limitations of the techniques for storing organs with a view to their transplantation, it is an object of the present invention to make available a solution for conserving organs, in particular hearts, by perfusion, which is simple to implement but at the same time permits considerably longer storage time compared to the existing techniques.

Another object of the invention is to make available a solution for organ storage which is inexpensive and which allows a reduction in the overall costs of transplantation.

According to the invention, these objects are achieved by virtue of a method for hypothermic perfusion of a cardiac organ, characterized in that:

a) the cardiac organ to be perfused is placed in a first tank, which is refrigerated and sealed and which communicates with pressurizing means, said tank containing a physiological liquid for storage, b) the organ to be perfused is attached by an artery to a nozzle communicating with a second tank, which is provided with an overflow outlet to the first tank, which overflow outlet is equipped with a non-return valve, c) the first tank is intermittently pressurized by way of the pressurizing device in order to perform retrograde pulsatile perfusion, comprising successively at least:

i. a "systole" phase of the cardiac organ during the pressurization of the first tank, in the course of which the physiological liquid penetrates the cavities of the cardiac organ, the perfusate being evacuated into the second tank via the artery communicating with the nozzle, and ii. a "diastole" phase of the cardiac organ when the first tank is not pressurized, in the course of which the perfusate contained in the second tank exerts a hydrostatic pressure in the artery connected to the nozzle and irrigates the organic tissue.

The hypothermic perfusion method according to the invention provides a novel solution for storing organs that are to be transplanted, particularly heart transplants, and has several advantages over the known techniques. Firstly, the method according to the invention makes it possible to considerably extend the period of storage of the hearts that are to be transplanted. In particular, this makes it possible in practice to at least double the period of storage compared to storage techniques involving hypothermic immersion and, in some cases, to maintain the viability of the organ for up to 24 hours after its removal.

Secondly, the method according to the invention proves very simple and inexpensive to implement. It also permits a reduction in the overall cost of transplantation because of the extended period of storage that it permits, which somewhat reduces the urgency that characterizes current transplantation procedures.

Moreover, the perfusion method according to the invention also allows measurements to be carried out directly on the removed cardiac organ in order to assess its viability, especially by examination of the perfusate pressures at the entry and exit points of the organ.

In the method according to the invention, the pressure for pressurizing the first tank in the "diastole" phase is advantageously between 5 and 15 cm $H_2O$.

Moreover, in the context of the invention, the physiological liquid that is chosen and used can be a non-sanguineous or sanguineous liquid. In practice, a non-sanguineous liquid will be preferred. Moreover, advantageously, this physiological liquid is also ionically osmotic.

Preferably, in order to ensure that the organ to be transplanted is stored in optimal conditions, the first tank is kept at a temperature of between 2° C. and 8° C. This temperature corresponds to the ideal temperature for storage of the organ.

In a preferred embodiment of the method according to the invention, the perfused organ is a non-beating heart, connected by the aorta to the nozzle for communicating with the second tank. In fact, the method according to the invention has been specifically developed and refined for the storage and the transplantation of heart transplants, if appropriate from elderly patients, or even from recently deceased patients, something which is never done at present for heart transplants.

In this particular context of the storage and perfusion of a heart transplant, the physiological liquid is advantageously filtered at the entry of the left atrium during the "systole" phases.

According to another advantageous feature of the method according to the invention carried out on a non-beating heart, a hydrostatic pressure is exerted in the aorta during the "diastole" phases, the pressure causing the closure of the aortic valves and the retrograde perfusion of the myocardium via the coronary vessels, the perfusate that has irrigated the organ being evacuated into the first tank through the coronary sinus via the right atrium.

Also in the method according to the invention, in a preferred embodiment thereof, the coronary flow rate and the coronary resistance are measured during the "diastole" phases by way of sensors positioned in the second tank. Such measurements advantageously provide information on the viability of the perfused organ with a view to its transplantation.

The invention also relates to providing a device for hypothermic perfusion of a cardiac organ, which device is suitable for carrying out the perfusion method set out above. Thus, this particular device has:
  a. a first sealed tank able to contain a physiological liquid;
  b. a second sealed tank communicating, in a sealed manner, with the internal volume of the first tank via a nozzle;
  c. means for refrigerating the first tank and keeping the latter at a substantially constant temperature;
  d. means for intermittently pressurizing the internal volume of the first tank.

According to the invention, the second tank has a safety outlet provided with a non-return valve communicating with the first tank.

Also according to the invention, the second tank has an outlet for an internal overpressure, which outlet is provided with a filter and with a non-return valve.

Advantageously, the pressurizing means have an air compressor assembly connected in a sealed manner to the internal volume of the first tank by way of a suitable channel.

Also according to the invention, the air compressor assembly has a compressed-air generator, which delivers a substantially constant air flow and which is connected to a solenoid valve controlled by a pressure regulator in order to feed the first tank discontinuously via said channel and perform intermittent pressurization of said tank.

Also advantageously, the solenoid valve and the pressure regulator are powered by a battery or from the mains.

Finally, the second tank can have pressure sensors for measuring the coronary flow rate and the coronary resistance.

Various other features will become clear from the following description and by reference to the attached drawings which show non-limiting examples of embodiments of the subject matter of the invention.

BRIEF DESCRIPTION OF THE DRAWINGS

In the attached figures.

DETAILED DESCRIPTION

Figure 1:
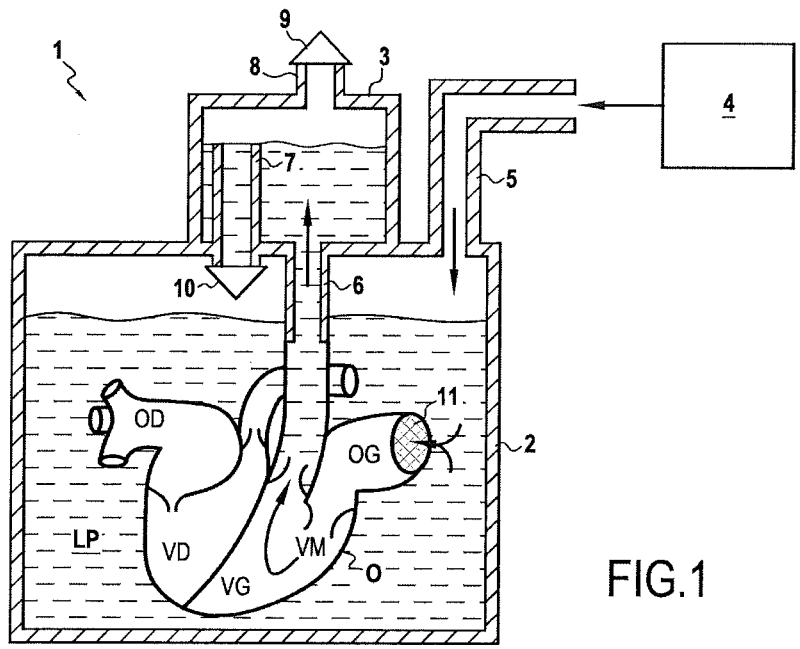
FIG. 1 shows a perfusion device according to the invention during a "systole" phase of a heart.
Figure 2:
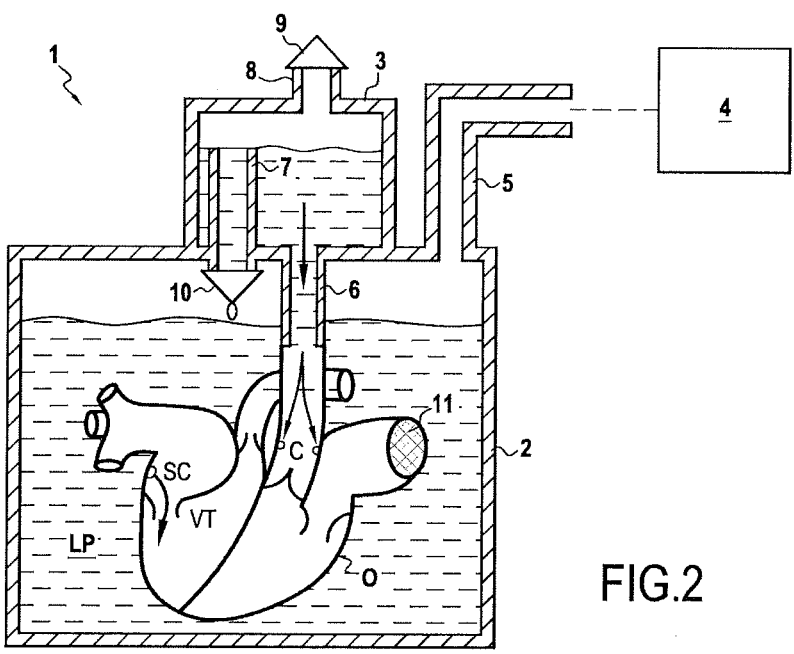
FIG. 2 is an illustration similar to that of FIG. 1, but during a "diastole" phase of the heart.

FIGS. 1 and 2 show a preferred embodiment of device 1 for hypothermic perfusion of organs in accordance with the invention. In these two figures, the perfusion device 1 contains an organ O perfused by means of the device 1, this organ being a non-beating heart in the case illustrated. However, the device 1 is not limited to the perfusion of hearts and can also be used for the hypothermic perfusion of other organs.

The perfusion device 1 of the invention has a first sealed tank 2, on which is mounted a second tank 3 which is also sealed and which communicates with the first tank 2 by way of a nozzle 6 forming a cannula to which the organ O to be perfused is attached, the organ O being immersed in a physiological liquid LP contained in the first tank 2.

The first tank 2 also communicates with a pressurizing device 4 by way of a conduit 5 connecting the interior of the first tank 2 to the pressurizing device, so as to permit the pressurization of the internal volume of the first tank 2, and of the physiological liquid inside the latter, in order to perform perfusion of the organ O.

The first tank 2 is equipped with or cooperates with refrigeration means (not shown) keeping this tank and the physiological liquid LP contained therein at a temperature of 2° C. to 8° C., preferably a temperature of the order of 4° C., and if possible substantially constant.

Above the first tank 2, the second tank 3 constitutes a U-type perfusion system which, in its bottom wall common with the upper wall of the first tank 2, is provided with a safety element 7 formed by an overflow outlet duct which communicates with the first tank 2 and is equipped with a non-return valve 10. The second tank 3 also has an outlet element 8 for internal overpressure, provided with a filter and with a non-return valve 9, which are arranged in its upper wall. The second tank, the conduit 6 and the overflow outlet 7 thus form a device for U-type circulation of the physiological liquid LP between the first tank 2 and the second tank 3, permitting the perfusion of the organ O, as will be described below.

The pressurizing device 4 can be of any type permitting intermittent pressurization, at a controlled pressure, of the internal volume of the first tank 2. In a preferred embodiment, this device 4 has an air compressor assembly connected in a sealed manner to the internal volume of the first tank 2 via the conduit 5. The compressor assembly advantageously has a compressed-air generator delivering a substantially constant flow of air and connected to a solenoid valve controlled by a pressure regulator, in order to feed the first tank 2 discontinuously via the channel 5 and perform intermittent pressurization of said tank. Advantageously, the solenoid valve and the pressure regulator are powered by a battery of accumulators or from the mains electricity.

Alternatively, the pressurizing device can also be formed by a compressed-air cylinder provided with a flow-rate reducer delivering a constant flow of compressed air of approximately 250 ml/min (or 360 liters per 24 hours of operation). A solenoid valve has one input and 2 outputs, of which one escape output to the outside, monitored by a pressure regulator having two pressure references (0 and 100 mmHg). The assembly made up of solenoid valve and pressure regulator serves to feed the first tank 2 discontinuously with gas at a pressure defined by the pressure regulator.

Irrespective of the structure of the pressurizing device, the function of the latter is to activate and maintain the perfusion of the organ O in the first tank 2 according to a principle of intermittent retrograde perfusion at an assigned pressure with recycling of the medium.

The invention in fact proposes the use of a method for perfusion of the organ O similar to the physiological perfusion of the organs in the human body.

This method of perfusion proceeds as follows.

First of all, the organ O, in the example shown a non-beating heart to be perfused and transplanted, is placed in the physiological liquid LP in the first tank 2 of the perfusion device 1, kept cold at a temperature of about 4° C. This physiological liquid LP is preferably an ionically osmotic, non-sanguineous liquid commonly employed in the medical field.

The organ O is then attached via an artery, for example the aorta in the case of a heart, to the lower end of the conduit 6 connecting the first tank 2 and second tank 3.

Once the organ has been attached, the pressurizing device 4 is then activated in order to exert pulsatile perfusion of the physiological liquid LP in the tank 2 and thus perfuse the organ O. A distinction is thus made between two successive and separate phases of perfusion of said organ O, these two phases being shown schematically in FIGS. 1 and 2.

The first phase of perfusion is a phase with an overpressure inside the tank 2 and called the "systole" phase. In the sealed tank 2, the pressurizing device 4 creates an overpressure of between 5 and 15 cm $H_2O$, which is transmitted to the physiological liquid LP, which penetrates the organ O and thus has a massaging effect: the liquid enters the left atrium OG, which is provided with a filter 11, accesses the left ventricle VG by way of the open mitral valve VM, passes through the aortic valve and then flows via the conduit 6 into the second tank 3. This tank 3 is equipped with the conduit 7, which defines a constant and maximum level of the perfusate in this second tank (assigned perfusion pressure). The non-return valve 10 fixed on the lower end of the conduit 7 ensures the seal with respect to the first tank 2.

The systole phase is followed by a decompression phase called the "diastole" phase.

During this second phase, the pressurizing device 4 no longer exerts any pressure in the first tank 2. The perfusate or physiological liquid LP contained in the second tank 3 then exerts a hydrostatic pressure in the aorta of the heart O via the conduit 6. This hydrostatic pressure causes the closure of the aortic valves, and the myocardium then undergoes retrograde perfusion via the coronary vessels C, thus imitating a physiological diastole. The perfusate then irrigates the cardiac tissue before regrouping to exit the coronary sinus SC. It is then recycled, leaving either through the venae cavae or the tricuspid valve VT via the pulmonary artery into the first tank.

The excess perfusate in the tank 3 drops back into the first tank 2 via the conduit 7.

Thus, with the method and the device 1 for perfusion according to the invention, it is possible to store an organ O, such as a non-beating heart, by performing intermittent hypothermic perfusion thereof, by which means it is possible to extend the storage time of the organ O with a view to its transplantation. The perfusion performed is pulsatile and thus corresponds to the physiological perfusion, and this favors the preservation of the organ. This pulsatility ensures a massaging of the organ O and circulation of the perfusate in the organ through the interplay of overpressure and underpressure provided by the device 1 and its pressurizing device.

Moreover, the perfusion device 1 according to the invention ensures permanent debubbling of the physiological liquid and of the organ by virtue of the "diastole" mechanism maintained solely by gravity following the assigned overpressures. This represents an essential advantage of the method and device according to the invention, since it eliminates the risks of embolisms and also a continuous perfusion through organic tissue.

When the perfused organ is a heart, as in the example shown in the figures, the perfusion method of the invention, in a particular embodiment, furthermore involves measuring the coronary flow rate and the ventricular compliance during the "diastole" phases. This measurement can be carried out by way of sensors positioned in the second tank 3.

The invention thus proposes a perfusion method and device which are simple and can be applied directly to the clinical procedures for storage of organs with a view to their transplantation, and which make it possible to considerably extend the period of storage of the organs between their harvesting and their transplantation.

The invention is not limited to the examples described and illustrated, since various modifications can be made without departing from the scope of the invention.

The invention claimed is:

1. A device (1) for hypothermic perfusion of a cardiac organ comprising:
   a. a first sealed tank (2) able to contain a physiological liquid (LP);
   b. a second sealed tank (3) communicating, in a sealed manner, with an internal volume of the first tank via a nozzle (6), an end of the nozzle adapted to connect to the cardiac organ;
   c. a device for refrigerating the first tank (2) and keeping the first tank (2) at a substantially constant temperature;
   d. a device (4) for intermittently pressurizing the internal volume of the first tank;
   wherein the first tank (2) communicates with the pressurizing device (4) by way of a conduit (5) connecting an interior of the first tank (2) to the pressurizing device, so as to permit pressurization of the internal volume of the first tank (2) and of the physiological liquid inside the first tank (2), in order to perform perfusion of the organ (O); and
   wherein the second tank (3) constitutes a U-type perfusion system which, in a bottom wall thereof common with an upper wall of the first tank (2), comprises a safety element (7) formed by an overflow outlet duct which communicates with the first tank (2) and includes a non-return valve (10).

2. The device as claimed in claim 1, comprising where the second tank (3) has an outlet (8) for an internal overpressure, which outlet (8) is provided with a filter and with a non-return valve (9).

3. The device as claimed in claim 1, comprising where the pressurizing means (4) have an air compressor assembly connected in a sealed manner to the internal volume of the first tank (2) via a suitable channel (5).

4. The device as claimed in claim 3, comprising where the air compressor assembly has a compressed-air generator, which delivers a substantially constant air flow and which is connected to a solenoid valve controlled by a pressure regulator in order to feed the first tank discontinuously via said channel and perform intermittent pressurization of said tank.

5. The device as claimed in claim 4, comprising where the solenoid valve and the pressure regulator are powered by a battery or by mains.

6. The device as claimed in claim 1, comprising where the second tank (3) has sensors for measuring the coronary flow rate and the coronary resistance of a cardiac organ (O).

* * * * *